United States Patent [19]

Ito et al.

[11] Patent Number: 5,772,960
[45] Date of Patent: Jun. 30, 1998

[54] CONTAINER FOR MEDICAL USE

[75] Inventors: Takushi Ito, Mitaki-Honmachi; Kouji Suzuki, Misasa-Kitamachi; Norihiko Kobayashi, Hatsukaichi, all of Japan

[73] Assignee: JMS Co., Ltd., Hiroshima, Japan

[21] Appl. No.: 753,930

[22] Filed: Dec. 3, 1996

[30] Foreign Application Priority Data

Dec. 4, 1995 [JP] Japan .................................. 7-339991

[51] Int. Cl.⁶ .......................... A61B 19/00; B01J 19/00; G01N 33/00
[52] U.S. Cl. ........................ 422/41; 422/48; 604/262; 604/408; 604/409; 604/410
[58] Field of Search ................... 604/410, 408, 604/409, 262; 422/41, 48

[56] References Cited

U.S. PATENT DOCUMENTS 4,132,594  1/1979  Bank et al. .......................... 195/1.8
4,657,542  4/1987  Ohachi ............................... 604/410
4,837,047  6/1989  Sato et al. ........................... 422/41

FOREIGN PATENT DOCUMENTS 2-42503  4/1989  Japan .

*Primary Examiner*—Laurie Scheiner
*Attorney, Agent, or Firm*—Cummings & Lockwood

[57] ABSTRACT

Containers for medical use comprising a storage portion formed of a soft polyvinyl chloride resin containing a vinyl chloride resin and diundecyl pthalate (DUP) as a plasticizer wherein the sheet exhibits an oxygen permeability of about $9.0 \times 10^{-10}$ to $22.0 \times 10^{-10}$ cc.cm/cm2.sec.cmHg/22° C. and a carbon dioxide permeability of about $6.0 \times 10^{-9}$ to $19.0 \times 10^{-9}$ cc.cm/cm2.sec.cmHg/22° C. The containers are suitable for the storage of blood, especially the cellular components of blood. The invention also provides processes for making such containers as well as methods for storing blood cells using such containers.

16 Claims, 1 Drawing Sheet

CONTAINER FOR MEDICAL USE

FIELD OF THE INVENTION

The present invention relates to improved containers for medical use. More specifically, the present invention relates to containers made of vinyl chloride resin and which are used for the extended storage of blood and the cellular components of blood.

BACKGROUND OF THE INVENTION

The increased use of blood component transfusion in place of whole blood transfusion and the concomitant use of related procedures such as apheresis has created a need for containers that are particularly suitable for the extended storage of whole blood and its cellular components.

The need exists especially for containers that maintain the viability of the stored blood cells. It is known that the viability of cells during storage is very much influenced by the gas permeability of the containers. For example, when platelet concentrates (hereinafter referred to as PC) are stored in standard containers made of vinyl chloride resin, the pH is notably reduced due to the low gas permeability of the containers. This in turn leads to deterioration of platelet function. Accordingly, the platelets can be stored only for limited periods of time following collection. This of course creates logistical problems for medical institutions, blood centers, blood donors and recipients and the like.

One way to improve the gas permeability of containers is to increase the amount of plasticizer that is normally added to the vinyl chloride resin. However, because the commonly used plasticizers, including DEHP (di-2-ethylhexyl phthalate), exhibit high levels of plasticizability, the use of large amounts of plasticizers causes difficulties in the molding and processing of the vinyl chloride resin. For this reason, the amount of plasticizer added to the vinyl chloride resin has to be limited. But the plasticizers when used in such limited amounts do not provide the levels of gas permeability required for long term storage of blood components. Furthermore, it has been reported that many of the known plasticizers, especially DEHP, are not blood compatible. For example, the use of these agents is known to correlate with suppressed aggregation and function of platelets. Additionally, it is known that ordinary plasticizers such as DEHP are eluted from the storage container into the stored blood or blood components. In consideration of the above factors, the use of large amounts of the known plasticizers in the construction of blood storage containers is not desirable.

Another common method of increasing gas permeability of containers is to use certain polyolefin resins instead of vinyl chloride resins. Polyolefins offer the additional advantage of not requring the use of plasticizers which, as discussed above, often elute from the container into the stored material. However, we found that containers made of polyolefins were not highly desirable for blood storage because they led to increased adhesion of blood cells when compared to vinyl chloride resin containers. Moreover, the moldability and processability of polyolefin containers is inferior to those made of vinyl chloride resin. Finally, the cost of polyolefin resin is higher than that of vinyl chloride resin. For these reasons, polyolefin containers are not preferable over vinyl chloride containers for blood storage.

Other defects associated with the conventional containers made of soft vinyl chloride resins are decreased flexibility and decreased mechanical strength at low temperatures. For example, when conventional blood bags formed of vinyl chloride resin are frozen at $-20°$ C., many of the bags become ruptured. Accordingly, care must be taken when blood cells or plasma are stored frozen. Additionally, at $4°$ C., which is the preferred temperature for erythrocyte storage, the flexibility of blood bags formed of vinyl chloride resins decreases and the bags become difficult to handle.

In view of the deficiencies of the known containers, efforts have been made to construct containers that would improve cell viability and which are made of vinyl chloride resin which is less costly and which exhibit better moldability and processability than other materials. These approaches have also included the changing of the type of plasticizer blended with the resin. Diundecyl phthalate (DUP) which is used in the present invention is not easily absorbed into vinyl chloride resin when compared to DEHP. Accordingly, DUP does not mix uniformly with vinyl chloride resin. When the plasticizer does not uniformly mix with the vinyl chloride resin, it is difficult to mold and process the resin, and the plasticizer easily elutes from the surface of the molded article. Although DUP is superior to DEHP with respect to providing increased gas permeability as well as improving the mechanical strength of the molded article, it does not easily mix with vinyl chloride resin. For this reason, it was substantially difficult to use DUP in a product for medical use, especially a container for the collection and/or storage of whole blood or its components.

SUMMARY OF THE INVENTION

It is an object of the present invention to provide a container formed of a vinyl chloride resin suitable for the extended storage of blood and its cellular components. More specifically, the present invention provides a blood storage container (especially a platelet storage container) which exhibits excellent cell viability and blood compatibility when blood cells (especially platelets) are stored for long periods of time. The present inventors have found that when a specific vinyl chloride resin is used, increased amounts of DUP can be blended with the vinyl chloride resin. It has been further found that even when the vinyl chloride resin is mixed with DUP in a large amount within a predetermined range, the moldability and the processability of the resin do not deteriorate much, and that the resulting container retains the mechanical strength required for its function as a blood storage container. The container of the present invention consists of sufficient amount of DUP which contributes to its high gas permeability and flexibility. The increased flexibility improves cell dispersability when cells are stored with agitation for extended periods of time. The improved gas permeability in conjunction with the increase in flexibilty leads to prolonged cell viability. Additionally, the container of the present invention exhibits improved flexibility at low temperatures and improved impact resistance when frozen. Finally, the amount of a plasticizer eluted from the containers of this invention is small making them more blood compatible than previously known containers.

In one embodiment, the present invention provides a container for medical use comprising a storage portion formed of a sheet of soft polyvinyl chloride resin containing a vinyl chloride resin and DUP as a plasticizer wherein the sheet exhibits an oxygen permeability of about $9.0 \times 10^{-10}$ to $22.0 \times 10^{-10}$ cc.cm/cm2.sec.cmHg/$22°$ C. and a carbon dioxide permeability of about $6.0 \times 10^{-9}$ to $19.0 \times 10^{-9}$ cc.cm/cm2.sec.cmHg/$22°$ C. In order to obtain the above-mentioned gas permeability, DUP in an amount of about 50 to 120 parts by weight per 100 parts by weight of the vinyl chloride resin must preferably be used.

In a further embodiment a container having a combination of the above-mentioned construction and any one or more of the following chracteristics is provided. For example, the sheet forming the storage portion of the container, in addition to the above mentioned gas permeability, exhibits a hardness of about 20 to about 30 as measured according to JIS standard 7215, strength of about 1.2 to 1.6 kgf/mm2 as measured according to JIS standard 7113, and/or thickness of about 0.2 to 0.45 mm.

The present invention also provides a method for storing blood cells in which the cells are stored in the containers described above. This method is useful especially when the blood cells are platelets, and further when large amounts of platelets are stored or platelets are stored for long periods of time. For example, this method, used with or without additive solution, is useful when platelets are stored for 72 to 120 hours or when 5 to 20 units (1 unit contains $2 \times 10^{10}$) of platelets are stored. When 5 to 10 units of platelets are stored, it is preferable to use a container having a capacity of 600 ml. When 10 to 20 units of platelets are stored, it is preferable to use a container having a capacity of 800 ml. When 20 to 35 units of platelets are stored, it is preferable to use a container having a capacity of 1000 ml.

Additionally, the present invention provides a process for producing the containers for medical use as described above in the first aspect of invention. The process comprises mixing a vinyl chloride resin that easily absorbs DUP, and molding and processing the mixture. It is preferable to use a vinyl chloride resin having a porosity of from 10 to 50 cc/100 g PVC.

The process also comprises mixing a vinyl chloride resin having a porosity of about 20 to 40 cc/100 g PVC with DUP and molding and processing the mixture, wherein the amount of DUP may be between 70 to 100 parts by weight per 100 parts by weight of vinyl chloride resin and wherein the container may comprise a storage portion formed of a sheet of soft polyvinyl chloride resin containing a vinyl chloride resin and DUP as a plasticizer wherein the sheet exhibits an oxygen permeability of about $9.0 \times 10^{-10}$ to $22.0 \times 10^{-10}$ cc.cm/cm$^2$.sec.cmHg/22° C. and a carbon dioxide permeability of about $6.0 \times 10^{-9}$ to $19.0 \times 10^{-9}$ cc.cm/cm$^2$.sec.cmHg/22° C.

DETAILED DESCRIPTION OF THE INVENTION

Figure 1:
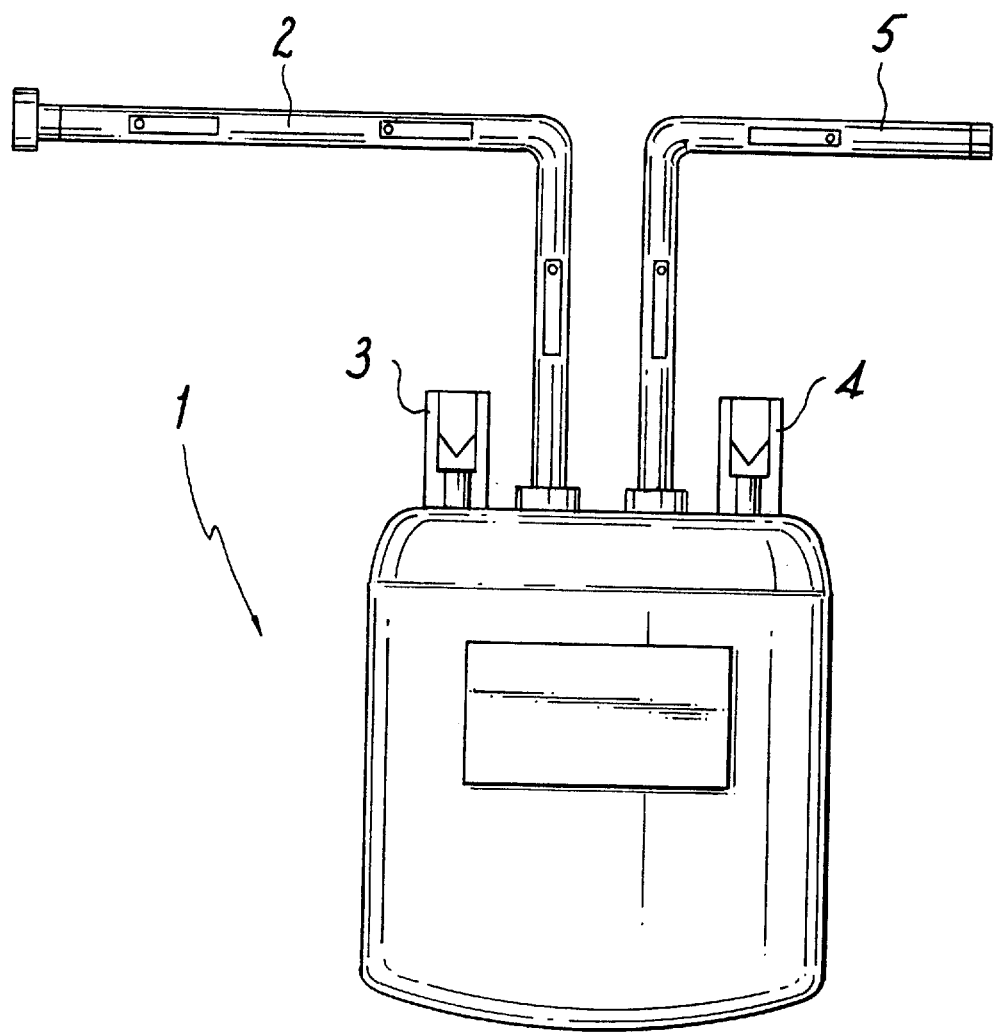
FIG. 1 shows a platelet storage container which represents a working example of the present invention. The container is formed of a vinyl chloride resin containing DUP. The platelet storage container 1 comprises a flexible collecting tube 2 connected with a blood collection container (not shown), transfusion apertures 3, 4 for transfusing the platelets, and a transfer tube 5 for withdrawing components separated from the platelet suspension stored in the platelet storage container.

Through experimentation, the present inventors have discovered that when a vinyl chloride resin having specific physical properties such as a porosity and the like is used, DUP can be absorbed well into the resin, and the vinyl chloride resin can be mixed easily and uniformly with DUP. They have also discovered that DUP exhibits low plasticizability compared to other plasticizers, and that even when DUP is blended with the vinyl chloride resin in a large amount within a predetermined range, moldability and processability of the resin do not deteriorate very much, and that the resulting container retains the strength necessary for its intended use. Due to the amount of DUP used, the containers of the present invention exhibit a high degree of gas permeability that is not achieved using other plasticizers. The increased gas permeability leads to prolonged viability of the cells stored in the containers of this invention. The amount of plasticizer used also increases the flexibility of the containers. Consequently, improved cell dispersability is observed when blood cells such as platelets and the like are stored in the containers of the present invention for long periods of time with agitation.

Due to the amount of plasticizer present, the containers of this invention remain flexible even at low temperatures and exhibit improved impact strength when frozen. Accordingly, the containers of the present invention may be used not only for platelet storage but also for the storage of erythrocytes at low temperatures or for storing plasma in a frozen state. These properties of the containers of the present invention also eliminate the need for the troublesome exchange of blood bags or the selection of a particular type of blood bag depending on factors such as the material to be stored, the storage method or the storage temperature. For example, there is a blood bag for component transfusion in which three bags are connected with a tube. This blood bag consists of a first bag for storing the whole blood collected (this is also a bag for fractionating the blood into components such as erythrocytes), a second bag for storing platelet suspensions, and a third bag for storing plasma. The three bags are interconnected before fractionating the blood. However, since the components to be stored are different from one another, the components are stored in individual bags, then separated, and stored under different conditions using different methods. Some of the components are stored in frozen state. Therefore, it would be preferable that the bags are formed of different materials. However, this is actually difficult and expensive. Under these circumstances, the container of the present invention can be used to store all of the components using different storing methods and different storage conditions.

In the containers of the present invention, the amount of plasticizer that elutes into the stored material is smaller than that observed in containers made using the same amount of other plasticizers. Accordingly, the containers of the present invention alleviate the undesirable effects of plasticizer elution such as damage to the cellular components of the stored blood and the resulting impairment of function. This decrease in plasticizer elution observed in the containers of the present invention make them particularly suitable for blood storage i.e., make them blood compatible.

As stated above, when DUP is used as the plasticizer to be blended with the vinyl chloride resin, a higher degree of gas permeability than which is obtained with the use of conventional plasticizers is seen. Also, with DUP the flexibility of the containers is so enhanced as to increase the dispersibility of the cells stored in the containers. The increased gas permeability and flexibility contribute to the increased cell viability seen with the use of the containers of this invention. The use of DUP also reduces the amount of plasticizer eluted, thereby improving the blood compatibility of the containers. Finally, the containers of this invention remain flexible even at a low temperatures and exhibit improved impact strength when frozen thereby reducing the incidents of breakage often noted with the use of containers made with conventional plasticizers.

In order to impart the gas permeability and the flexibility required for the containers for medical use of the present invention, it is preferable that at least 50 parts of DUP plasticizer per 100 parts by weight of the polyvinyl chloride but no more than 130 parts by weight be used. It should be noted that it is difficult to blend more than 60 parts by weight of DEHP, a conventional plasticizer, with polyvinyl chloride. When the amount of the plasticizer to be blended with polyvinyl chloride is too small, the gas permeability or the flexibility of the resulting container is not sufficient for its medical use. Meanwhile, when it is too large, the vinyl chloride resin becomes difficult to mold and process, and the mechanical strength of the resulting container does not reach satisfactory levels. Further, when the plasticizer is present in an excessive amount, the plasticizer tends to be easily eluted from the surface of the container. For these reasons, the amount of DUP should preferably be between about 50 and 120 parts by weight, more preferably between about 70 and 100 parts by weight per 100 parts by weight of the vinyl chloride resin.

The gas permeability of the container is influenced by the thickness of the sheets forming the storage portion of the containers, and the capacity and the inner surface area of the storage portion in the container.

For a platelet storage container in which the platelets are stored for about 72 to 120 hours, the sheet thickness should be preferably between about 0.20 and 0.45 mm, more preferably between about 0.32 and 0.42 mm. When the sheet thickness is less than 0.20 mm, the mechanical strength of the container is not sufficient for its intended medical use. For example, such a container will not withstand centrifugation or the rigors of transportation that blood cell storage containers are normally subjected to. Meanwhile, when the sheet thickness exceeds 0.45 mm, gas permeability is decreased, making it impossible to store platelets for a long period of time.

The optimum container size varies with the number of platelets to be stored. The optimum capacity of the platelet storage container for storing 5 to 10 units platelets (1 unit contains $2 \times 10^{10}$ platelets) for a long period of time is about 600 ml (inner size: 21 cm×14 cm), and the effective inner surface area thereof is preferably between about 600 and 700 $cm^2$. In order to store 10 to 20 units of platelets, a container having a capacity of about 800 ml (inner size: 21 cm×16 cm) and an effective inner surface area of about 700 to 800 $cm^2$ is preferable. In order to store 20 to 35 units of platelets, a container having a capacity of about 1000 ml (inner size: 28 cm×16 cm) and an effective inner surface area of about 800 to 1,000 $cm^2$ is preferable. When the capacity and the inner surface area of the storage container relative to the number of stored platelet units are too small, the optimal gas permeability cannot be obtained. When the capacity and inner surface area are too large, the container size also becomes large making the handling of the container difficult.

It is preferable that the sheet forming the blood cell storage container, especially the platelet storage container, exhibit an oxygen permeability of about $9.0 \times 10^{-10}$ to $22.0 \times 10^{-10}$ cc.cm/cm2.sec.cmHg/22° C. and a carbon dioxide permeability of from $6.0 \times 10^{-9}$ to $19.0 \times 10^{-9}$ cc.cm/cm2.sec.cmHg/22° C. When the gas permeability is too high, a large amount of oxygen permeates into the container to increase the pH of the plasma or additive solution which adversely affects the function of the stored cells.

Through experimentation, the present inventors have discovered that a blood storage container consisting of a larger amount of DUP allows lesser precipitation and adhesion of platelets stored therein. This is presumably because the container becomes more flexible with the increasing amount of plasticizer used and when stored with agitation the container flexes making it difficult for the cells to precipitate or adhere. Consequently, it is considered that when a predetermined amount of DUP is blended with polyvinyl chloride resin to form a container for medical use, not only is high gas permeability imparted to the container, but also the flexibility of the container is improved, and that the combination of these two effects leads to increased platelet viability. However, since the container for medical use is subjected to centrifugation, sterilization or the like, the container must possess a predetermined mechanical strength. It is, therefore, preferable that a storage container of blood cells such as platelets, erythrocytes and the like exhibit a hardness of from 20 to 30 as measured according to JIS standard K7215 and a strength of about 1.2 to 1.6 kgf/mm2 as measured according to JIS standard K7113. The above-mentioned hardness or strength is dependent upon and varies with the amount of added plasticizer and thickness of the sheets forming the storage container.

As discussed above, DUP is the plasticizer of choice for the making of the containers of the present invention. However, the type of vinyl chloride resin used may be selected from a variety of available resins so long as sufficient amount of DUP can be blended with the resin to produce containers having mechanical strength sufficient for their intended medical use. Examples of suitable resins include a homopolymer of vinyl chloride, a copolymer of vinyl chloride and another copolymerizable monomer such as vinylidene chloride, vinyl acetate, ethylene, propylene, styrene, acrylic acid, alkyl acrylate, acrylonitrile or metharcrylonitrile. Though the average degree of polymerization of the vinyl chloride resin is not particularly limited, it is preferably from about 1000 to 2500 in view of moldability, processability and strength.

It is not necessary that DUP be used as the sole plasticizer in this invention. DUP may be used with other types of plasticizers as long as the purpose of the invention is accomplished. However, the amounts of the other plasticizers used must be below 50% by weight of the whole PVC composites, preferably below 8% by weight of the whole PVC composite.

Since, in general vinyl chloride resin and DUP do not mix easily or uniformly, it is advisable to use a vinyl chloride resin to which DUP will adsorb easily. The adsorption of DUP to the vinyl chloride resin is influenced by various factors. One of the factors is the porosity of the vinyl chloride resin. The porosity of the vinyl chloride resin is preferably between 10 and 50 cc/100 g PVC, more preferably between 20 and 40 cc/100 g PVC. When the porosity of the vinyl chloride resin is less than 10 cc/100 g PVC, DUP is not easily adsorbed to the vinyl chloride resin. When the porosity is too high, the adsorption of DUP is improved, but the bulk specific gravity is reduced, impairing properties (for example, strength and moldability) of the vinyl chloride resin. When DUP is adsorbed into the vinyl chloride resin, the resin can easily be molded and processed. The uniform mixing of the resin and DUP is important since this will reduce the amount of plasticizer elution from the storage containers. The uniformity of the resin-plasticizer mix is also important in terms of controlling the quality and properties of the containers formed therefrom.

Another factor to take into consideration is the particle diameter of the vinyl chloride resin used to make the containers of this invention. Vinyl chloride resin having a larger particle diameter lends better flowability to the resin mixture and facilitates further treatment and handling steps. Generally, the particle diameter of the vinyl chloride resin should be between 50 and 250 $\mu$m, and preferably between 100 and 200 $\mu$m. Additionally, the vinyl chloride resin may contain, if needed, an epoxidized soya bean oil as a stabilizer and a plasticizer, a stabilizer such as calcium, zinc, stearic acid or lauric acid, and a lubricant, an antioxidant and the like.

In the above description the storage of platelets, for which gas permeability and flexibility of the storage container are considered crucial, has been emphasized. However, the containers of the present invention may also be used for storing whole blood as well as blood components such as erythrocytes, leukocytes, plasma, stem cells and the like. It should be noted that for the storage of erythrocytes and plasma it is not necessary to limit the gas permeability and flexibility of the storage portion of the containers to the above-specified ranges. Additionally, when the sheet thickness of the storage container for freezing or the storage portion for freezing is greater than that of the container for platelet storage and is set at about 0.4 to 0.5 mm the container does not rupture easily.

The following examples are set forth so that this invention may be better understood and are not to be construed as limiting its scope in any manner.

EXAMPLE 1

Materials and Methods

1. Molding of Container:

A 200-milliliter container for storing platelets was produced from a vinyl chloride resin sheet containing DUP in an amount of 65, 80 or 90 parts by weight per 100 parts by weight of a vinyl chloride resin, or from a polyolefin sheet. The film thickness of the sheet was set at 400 $\mu$m. In this case, S-1004 (Kanegafuchi Chemical Industry Co., Ltd.; degree of polymerization-1400; and porosity-28) was used as the vinyl chloride resin. The porosity of the vinyl chloride resin refers to the amount of mercury which is injected into 100 g of the resin using a mercury injection porosity meter (5-7118 Model, manufactured by Amino Co., USA) while absolute pressure is increased from 31 psi to 1011 psi. For comparison, a platelet storage container was formed using DEHP (di-2-ethylhexyl phthalate) as a plasticizer in an amount of 50 parts by weight per 100 parts by weight of the vinyl chloride resin. In addition, a container was formed of polyolefin also for comparison purposes. The DEHP and polyolefin containers had the same sheet thickness and capacity as the DUP-containing platelet storage containers.

2. Preparation of Platelet Concentrates:

Platelet concentrates (PC) having a predetermined concentration ($8.0 \times 10^5$ platelets/mm$^3$) were prepared by apheresis.

3. Evaluation of Cell Dispersibility of PC:

Approximately 150 ml of PC containing 6 units of human platelets (containing $1.2 \times 10^{11}$ platelets) was transferred into each of the above-formed containers. The containers were placed on a horizontal shaker set at 60 rpm/min and stored at 22° C. for 5 days. After 5 days of storage, the container surfaces were examined.

4. Measurement of Gas Permeability:

The gas permeability of the above containers was measured using the sheets used to form the platelet storage containers. The sheet was placed between a high pressure oxygen environment (0.5 kg/cm$^2$) and a low pressure oxygen environment (vacuum) and the amount of oxygen that migrated from the high pressure side to the low pressure side through the sheet was measured. The permeability of carbon dioxide was also measured by the same method. A gas permeability measuring device (GTR-10, manufactured by Yanaco) was used for this purpose.

RESULTS

Platelet Dispersability:

The platelet dispersability, measured by observation of platelet precipitation, in four types of storage containers is shown in Table 1. The greatest precipitation was observed in the polyolefin container and the least precipitation was seen in the polyvinyl chloride container formed with 90 parts by weight DUP (DUP 90). Furthermore it was noted that as the amount of DUP is increased, the precipitation and the adhesion of platelets decreased. It should be pointed out that decreased precipitation and adhesion lead to more efficient cellular metabolism, gas exchange and the like in the stored cells. The observed decrease in precipitation and adhesion is presumed to be the result of the greater flexibility of the containers caused by the use of increasing quantities of DUP. As discussed previously, the increased flexibility of containers that are stored with agitation reduces the precipitation and adhesion of the stored platelets.

TABLE 1

| CELL DISPERSABILITY | |
|---|---|
| CONTAINER TYPE | PLATELET PRECIPITATION |
| DUP65 | + |
| DUP80 | +/− |
| DUP90 | − |
| POLYOLEFIN | ++ |

[+ = Precipitation; − = no detectable precipitation; ++ = large amount of precipitation; +/− = small amount of precipitation]

Gas permeability:

The gas permeability of the platelet storage containers is shown in Table 2. As is clear from this table, the container formed of the vinyl chloride resin containing DUP is superior in gas permeability to the polyolefin container or the container formed of the vinyl chloride resin containing DEHP, and the container formed of the vinyl chloride resin containing DUP in a larger amount exhibits a better gas permeability.

TABLE 2

| GAS PERMEABILITY (cc · cm/cm2 · sec · cmHg/22° C.) | | |
|---|---|---|
| CONTAINER TYPE | OXYGEN | CARBON DIOXIDE |
| DUP65 | $9.5 \times 10^{-10}$ | $6.9 \times 10^{-9}$ |
| DUP80 | $1.3 \times 10^{-9}$ | $9.6 \times 10^{-9}$ |
| DUP90 | $1.5 \times 10^{-9}$ | $1.1 \times 10^{-8}$ |
| DEHP50 | $6.7 \times 10^{-10}$ | $3.4 \times 10^{-9}$ |
| Polyolefin | $3.1 \times 10^{-10}$ | $2.1 \times 10^{-9}$ |

EXAMPLE 2

Materials and Methods

1. Molding of containers:

The storage containers were prepared in the same manner as in Example 1.

2. Collection of platelet concentrates:

PC was prepared in the same manner as in Example 1.

3. Evaluation of platelet function:

The function of platelets after storage was evaluated in terms of the following parameters.

a.) Number of platelets

The number of platelets was measured using an automatic cell counter (Sysmex Model E-5000, manufactured by Toa Iyo Denshi K.K.)

b.) Plasma pH

The plasma pH was measured using a pH meter (EA-920, manufactured by K.K. Nikkaki).

c.) Hypotonic shock response

The hypotonic shock response indicates fragility of cells and ability to retain cell shape. The larger the value, the lesser the susceptibility of the platelet membrane to deformation. PC was diluted with water to render it hypotonic and spectrometric absorbance (OD=610 nm) of the diluted solution was measured by a spectrophotometer (UV160A, manufactured by Shimadzu Seisaku sho).

d.) Maximal aggregation induced by collagen

Maximal aggregation induced by collagen correlates with platelet function. The larger the value the more functional the platelets. Maximal aggregation was determined by adding collagen to each sample with a Hematolaser (manufactured by NKK).

e.) Lactate concentration

The lactate concentration indicates the cellular glucose consumption under anaerobic conditions. When the oxygen concentration is low, the lactate concentration increases.

RESULTS

Evaluation of a platelet function:

The results from the above assays are shown in Table 3. The results indicate that platelet function is better maintained in containers formed of DUP-containing vinyl chloride resin than in containers formed with DEHP-containing resin. Additionally, the results make clear that the amount of DUP in the resin is directly proportional to platelet function.

TABLE 3

EVALUATION OF PLATELET FUNCTION

| CONTAINER TYPE | Platelet counts ($\times 10^4$ cell/ml) | Plasma pH | % H S R (%) | Maximal Aggregation (%) | Lactate Concentration (g/l) |
|---|---|---|---|---|---|
| DUP65 | 69.3 | 6.63 | 39.2 | 65 | 1.85 |
| DUP80 | 73.3 | 6.99 | 59.3 | 80 | 1.22 |
| DUP90 | 76.6 | 7.33 | 66.3 | 82 | 0.94 |
| DEHP50 | 57.4 | 6.16 | 7.5 | 30 | 1.97 |
| 0 TIME | 80.0 | 7.13 | 70.0 | 86 | 0.024 |

[0 time = blood collected immediately after donation]

EXAMPLE 3

Materials and Methods

1. Molding of containers:

The storage containers were prepared in the same manner as in Example 1.

2. Measurement of container flexibility:

230 ml water was placed into each type of container and the containers were stored at 4° C. After 5 days, the container flexibility was determined by manual examination.

3. Test for breakage of frozen containers:

Each container was filled with 100 ml water and stored at −20° C. for 24 hours. The frozen containers were then dropped from a height of 1 meter and examined for breakage.

RESULTS

Container flexibility at low temperature:

As shown in Table 4, containers formed of the vinyl chloride resin containing DUP remain more flexible at 4° C. compared to the control containers formed of polyolefin or of vinyl chloride resin containing DEHP. Additionally, the data indicates that container flexibility at 4° C. is directly proportional to the amount of DUP in the vinyl chloride resin.

TABLE 4

CONTAINER FLEXIBILITY

| CONTAINER TYPE | 25° C. | 4° C. |
|---|---|---|
| DUP65 | + | +/− |
| DUP80 | ++ | + |
| DUP90 | ++ | + |
| DEHP50 | + | − |
| Polyolefin | +/− | − |

[++ = high flex; + = flex; +/− = low flex; − = stiff]

Breakage of frozen containers:

The results, shown in Table 5, indicate that containers formed of DUP-containing polyvinyl chloride resin were susceptible to less breakage than the control containers and that container breakage was inversely proportional to the amount of DUP used in the resin. Importantly, no breakage was observed when at least 80 parts by weight of DUP was present in the resin mixture.

TABLE 5

CONTAINER BREAKAGE

| CONTAINER TYPE | FREQUENCY OF BREAKAGE |
|---|---|
| DUP65 | 1/5 |
| DUP80 | 0/5 |
| DUP90 | 0/5 |
| DEHP50 | 2/5 |

[Temperature = −20° C.]

EXAMPLE 4

Materials and Methods

1. Molding of containers:

The containers were prepared as in Example 1.

2. Measurement of plasticizer elution:

The containers were filled with 200 ml of PC prepared as in Example 1 and stored at 22° C. for 120 hours. Then, 1 ml samples were removed for measurement of plasticizer elution. One ml of each blood sample was transferred to a flask and 10 ml of acetonitrile was added to each sample and the mixture shaken at 120 rpm/min for one hour. Each sample was then transferred to a centrifuge tube and centrifuged at 1500 g for one hour. The supernatant of each tube was then transferred to a flask and acetonitrile was removed by evaporation. Two ml of n-hexan was added to each flask and the flasks were shaken. Then 2 μl samples from the flasks were analyzed by gas chromatography.

RESULTS

Plasticizer elution:

As depicted in Table 6, very little plasticizer elution was noted in the containers formed of vinyl chloride resin containing DUP. Whereas, significant plasticizer elution was detected in the container formed of the DEHP-containing vinyl chloride resin.

TABLE 6

PLASTICIZER ELUTION

| CONTAINER TYPE | PLASTICIZER ELUTION (ppm) |
|---|---|
| DUP65 | <5 |
| DUP80 | <5 |
| DUP90 | <5 |
| DEHP50 | 100 |

While we have described above specific examples of this invention, it will be apparent to those of skill in the art that our basic methods may be modified without departing from the spirit of the invention. Therefore, the scope of the invention is to be defined by the claims appended hereto rather than by the specific examples presented above.

What we claim is:

1. A container for medical use comprising a storage portion formed of a sheet of soft polyvinyl chloride resin containing a vinyl chloride resin and DUP as a plasticizer wherein the amount of DUP is between 70 and 100 parts by weight per 100 parts by weight of vinyl chloride resin and wherein the sheet exhibits an oxygen permeability of about $9.0 \times 10^{-10}$ to $22.0 \times 10^{-10}$ cc.cm/cm$^2$.sec.cmHg/22° C. and a carbon dioxide permeability of about $6.0 \times 10^{-9}$ to $19.0 \times 10^{-9}$ cc.cm/cm$^2$.sec.cmHg/22° C.

2. The container of claim 1, wherein the hardness of the sheet is between 20 and 30 as measured according to JIS standard K7215.

3. The container of claim 1, wherein the strength of the sheet is between 1.2 and 1.6 fgf/mm$^2$ as measured according to JIS standard K7113.

4. A method of storing platelets comprising placing platelets in the container of claim 1.

5. The container of claim 1 wherein the amount of DUP is >80 to ≦100 parts by weight per 100 parts by weight of vinyl chloride resin.

6. The container of claim 1 wherein the vinyl chloride resin has a porosity of about 10 to 50 cc/100 g.PVC.

7. A process for producing a container, which comprises mixing vinyl chloride resin having a porosity of about 20 to 40 cc/100 g.PVC with DUP and molding and processing the mixture.

8. The process of claim 7, wherein the amount of DUP is between 70 to 100 parts by weight per 100 parts by weight of vinyl chloride resin.

9. The process of claim 8, wherein the container comprises a storage portion formed of a sheet of soft polyvinyl chloride resin containing a vinyl chloride resin and DUP as a plasticizer wherein the sheet exhibits an oxygen permeability of about $9.0 \times 10^{-10}$ to $22.0 \times 10^{-10}$ cc.cm/cm$^2$.sec.cmHg/22° C. and a carbon dioxide permeability of about $6.0 \times 10^{-9}$ to $19.0 \times 10^{-9}$ cc.cm/cm$^2$.sec.cmHg/22° C.

10. The method of claim 9, wherein the platelets are stored for about 72 to 120 hours.

11. The method of claims 9, wherein about 5 to 35 units of platelets are stored.

12. The method of claim 9, wherein about 5 to 10 units of platelets are stored in a container having a capacity of approximately 600 ml.

13. The method of claim 9, wherein about 10 to 20 units of platelets are stored in a container having a capacity of approximately 800 ml.

14. The method of claim 9, wherein about 20 to 35 units of platelets are stored in a container having a capacity of approximately 1000 ml.

15. The process of claim 7 wherein said vinyl chloride resin has a particle diameter of between 50 and 250 μm.

16. The process of claim 15 wherein said vinyl chloride resin has a particle diameter of between 100 and 200 μm.

\* \* \* \* \*